(12) United States Patent
Harberts et al.

(10) Patent No.: US 9,669,208 B2
(45) Date of Patent: Jun. 6, 2017

(54) SPIRALED WIRES IN A DEEP-BRAIN STIMULATOR PROBE

(75) Inventors: Dirk Willem Harberts, Eindhoven (NL); Ke Wang, Eindhoven (NL); Franciscus Paulus Maria Budzelaar, Eindhoven (NL); Hubert Cecile Francois Martens, Eindhoven (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 202 days.

(21) Appl. No.: 13/128,257

(22) PCT Filed: Nov. 9, 2009

(86) PCT No.: PCT/IB2009/054962
§ 371 (c)(1),
(2), (4) Date: May 9, 2011

(87) PCT Pub. No.: WO2010/055453
PCT Pub. Date: May 20, 2010

(65) Prior Publication Data
US 2011/0224765 A1      Sep. 15, 2011

(30) Foreign Application Priority Data
Nov. 13, 2008  (EP) .................................. 08168994

(51) Int. Cl.
*A61N 1/00*      (2006.01)
*A61N 1/05*      (2006.01)
(Continued)

(52) U.S. Cl.
CPC .............. *A61N 1/0534* (2013.01); *A61N 1/05* (2013.01); *A61N 1/3718* (2013.01); *A61N 2001/086* (2013.01); *H01B 7/048* (2013.01)

(58) Field of Classification Search
CPC .. A61N 2001/086; A61N 1/05; A61N 1/3718; A61N 1/0534; H01B 7/048
(Continued)

(56) References Cited

U.S. PATENT DOCUMENTS 4,845,429 A * 7/1989 Burreson ........... H03K 17/9537
                                              324/207.19
5,964,705 A   10/1999 Truwit
(Continued)

FOREIGN PATENT DOCUMENTS

WO    2006023700 A2   3/2006
WO    2007118194 A2   10/2007
(Continued)

OTHER PUBLICATIONS

Patrick Scoggins, A Guide to Designing Copper-Foil Inductors, Jul. 1, 2007, http://powerelectronics.com/passive_components_packaging_interconnects/magnetics/copper-foil-inductor-design-guide-0707/ , Accessed on Jul. 2, 2012.*
(Continued)

*Primary Examiner* — Lindsey G Wehrheim
(74) *Attorney, Agent, or Firm* — Shumaker & Sieffert, P.A.

(57) ABSTRACT

The present invention regards a probe for deep brain stimulation (DBS), with high overall impedance, but low overall resistance. This is achieved since the probe comprises a structure comprising at least two interconnected spirals, wherein said two spirals have different direction of rotation. A system for deep brain stimulation comprising the probe, a power source and an electrode is also disclosed.

18 Claims, 5 Drawing Sheets

(51) Int. Cl.
*H01B 7/04* (2006.01)
*A61N 1/37* (2006.01)
*A61N 1/08* (2006.01)

(58) Field of Classification Search
USPC .......................................... 607/115, 116, 126
See application file for complete search history.

(56) References Cited

U.S. PATENT DOCUMENTS

| | | | |
|---|---|---|---|
| 6,343,226 B1* | 1/2002 | Sunde et al. .................. | 600/378 |
| 6,757,970 B1* | 7/2004 | Kuzma et al. .................. | 29/847 |
| 7,174,219 B2 | 2/2007 | Wahlstrand et al. | |
| 2003/0083726 A1* | 5/2003 | Zeijlemaker et al. ........ | 607/122 |
| 2004/0147992 A1* | 7/2004 | Bluger et al. ................. | 607/116 |
| 2005/0222647 A1 | 10/2005 | Wahlstrand | |
| 2005/0222656 A1* | 10/2005 | Wahlstrand et al. ......... | 607/116 |
| 2005/0222658 A1 | 10/2005 | Hoegh et al. | |
| 2006/0030774 A1* | 2/2006 | Gray et al. .................... | 600/435 |
| 2006/0206185 A1* | 9/2006 | Schuller ........................ | 607/137 |
| 2006/0247748 A1 | 11/2006 | Wahlstrand et al. | |
| 2008/0119917 A1 | 5/2008 | Geistert | |
| 2008/0129435 A1 | 6/2008 | Gray | |
| 2008/0243218 A1* | 10/2008 | Bottomley et al. ........... | 607/116 |
| 2008/0262584 A1* | 10/2008 | Bottomley ............... | A61N 1/05 |
| | | | 607/119 |

FOREIGN PATENT DOCUMENTS

| | | |
|---|---|---|
| WO | 2008115426 A1 | 9/2008 |
| WO | 2011010257 A1 | 1/2011 |

OTHER PUBLICATIONS

Scoggins, Patrick; A Guide to Designing Copper-Foil Inductors; Power Electronics Technology; Jul. 2007; pp. 30-34.
Office Action dated Mar. 25, 2013 from Chinese Application No. 200980145345.
Official Action dated Sep. 30, 2014 for European Patent Application No. 09 759 816.3.

* cited by examiner

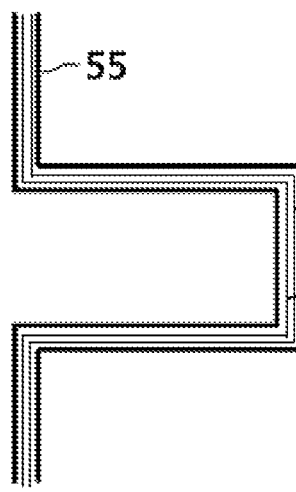 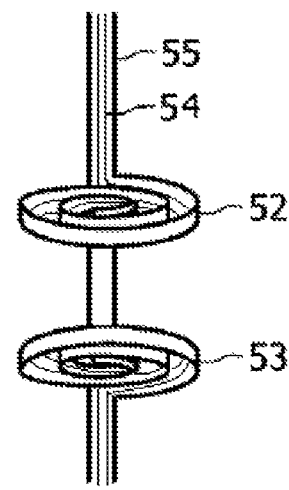
FIG. 8A          FIG. 8B
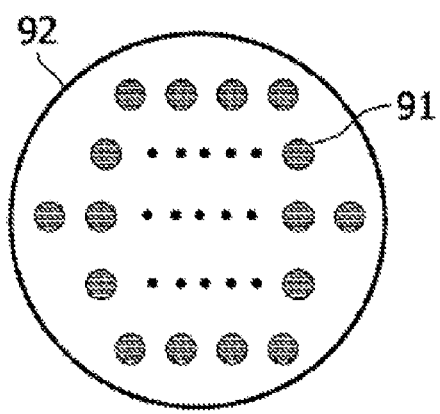
FIG. 9

SPIRALED WIRES IN A DEEP-BRAIN STIMULATOR PROBE

FIELD OF THE INVENTION

The present invention relates to a probe for deep brain stimulation (DBS). More specifically, the present invention relates to a probe suitable for use even under influence of a strong external magnetic field.

BACKGROUND OF THE INVENTION

Within the field of neurotechnology, deep brain stimulation (DBS) is a surgical treatment involving the implantation of a medical device called a deep-brain stimulator, which sends electrical impulses to specific parts of the brain. DBS in certain brain regions has provided remarkable therapeutic benefits for otherwise treatment-resistant disorders such as chronic pain, Parkinson's disease, tremor and dystonia. Despite the long history of DBS, its underlying principles and mechanisms are still not clear. DBS directly changes brain activity in a controlled manner. Unlike lesioning techniques, its effects are reversible. Furthermore, DBS is one of only a few neurosurgical methods that allow blinded studies.

FIG. 1 illustrates an example of a DBS system 10 according to prior art. In principle, the DBS system comprises two components, illustrated by FIG. 1: the implanted pulse generator (IPG) 11, and the probe 12. The IPG 11 is a battery-powered neurostimulator that sends electrical pulses to the brain to interfere with neural activity at the target site. The IPG 11 is typically encased in e.g. a titanium housing. The probe 12 consists of about 10-15 cm long wires and a plurality of electrodes. The wires connect the IPG to the electrodes 13, which are located at the distal end of the probe. The IPG may be calibrated by a neurologist, nurse or trained technician to optimize symptom suppression and control side effects.

DBS probes are placed in the brain according to the type of symptoms to be addressed. All components are surgically implanted inside the body. The typical procedure is performed under local anesthesia, where a hole is drilled in the skull and the electrode is inserted with feedback from the patient for optimal placement. The right side of the brain is stimulated to address symptoms on the left side of the body and vice versa. FIG. 2 is illustrating how a DBS system 10 may be positioned in the brain of a person 21. FIG. 3 illustrates how two DBS systems 10 may be positioned in the brain of a person 31, to stimulate both left and right side of the body of person 31.

When a person with a DBS probe undergoes an examination with magnetic resonance imaging (MRI), a strong electric field may result near the end of the probe as a result of the electromagnetic field coinciding with the probe. This electric field induces currents that heat up the brain tissue. Excessive heating may destroy the brain tissue. For example, it has been shown that for an insulated, 20 cm long straight wire, the temperature in surrounding tissue may increase to 48° C. in the normal operating mode of an 1.5 T MRI system. In contrast, only temperature increases less than 1° C. are considered safe.

In order to resolve the problem of induced currents and thus undesired heating of human tissue, high impedance probes have been suggested. Simulations indicate that the overall impedance of a probe should be at least 1 kΩ for the current to be sufficiently low, consistent with Ohm's law. However, such high impedance leads to a very limited battery life. By configuring a probe with a number of parallel electrically conducting leads, having a spiral form, the battery life may be increased, since the overall impedance of such a probe is the sum of the impedance of all the interconnect leads, e.g. electrical conducting wires in parallel. For instance, the overall impedance of 50 parallel leads with individual impedance of 1 kΩ is 20Ω.

FIG. 4 is showing an internal view of the probe 12 according to prior art, wherein a number of electrically conducting leads 41 run from a first end 42 of said probe to electrodes 13, which are located at the distal end of the probe. In use, the probe 40 is connected at the first end 42 to a power source and electronics, such as an IPG, enabling an electric current to flow through said electrically conducting leads 41 to the electrodes 13.

However, due to the spiraling form of the electrically conducting leads 41, high voltages and/or currents are resulting in the electrically conducting leads, when the probe is subjected to an external magnetic field, such as when performing MRI. Thus, there is a risk that the electronics of the IPG, connected to the electrically conducting leads 41, is damaged when the spiraled conducting leads 41 are subjected to an external magnetic field.

Hence, an improved DBS probe allowing for increased flexibility, cost-effectiveness, sufficiently long battery life, safe operation of electronics and prevention of excessive heating of tissue during MRI examination would be advantageous.

SUMMARY OF THE INVENTION

Accordingly, the present invention preferably seeks to mitigate, alleviate or eliminate one or more of the above-identified deficiencies in the art and disadvantages singly or in any combination and solves at least the above mentioned problems e.g. by providing a probe for Deep Brain Stimulation (DBS).

In an aspect, the probe comprises a number of electrically conducting leads forming a structure. The structure comprises at least two interconnected spirals wherein said two spirals have different direction of rotation.

This gives the advantage that the probe may be used in conjunction with an external magnetic field with altering polarity without excessive heating of surrounding tissue. The different direction of rotation of the spirals also prohibits occurrence of high voltages and/or currents the electrically conducting leads, when the probe is subjected to an external magnetic field, such as when performing MRI. Thus safe operation of electronics connected to the probe is achieved. Furthermore, it allows increased flexibility, cost-effectiveness, and sufficiently long battery life.

In another aspect, a system for deep brain stimulation comprising the probe is provided.

In yet another aspect, a pacemaker system comprising the probe is provided.

In another aspect, a muscle stimulation system comprising the probe is provided.

In yet another aspect, a system for gastro-intestinal stimulation comprising the probe with a number is provided.

In a further embodiment, use of the probe for deep brain stimulation is provided.

Other embodiments and advantages will be explained in further detail below.

BRIEF DESCRIPTION OF THE DRAWINGS

These and other aspects, features and advantages of which the invention is capable of will be apparent and elucidated from the following description of embodiments of the present invention, reference being made to the accompanying drawings, in which;

FIG. 8 is an illustration of showing rotation according to an embodiment; and FIG. 9 is an illustration of a cross-section of a probe according to an embodiment.

DESCRIPTION OF EMBODIMENTS

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

The following description focuses on an embodiment applicable to deep brain stimulation.

Figure 1:
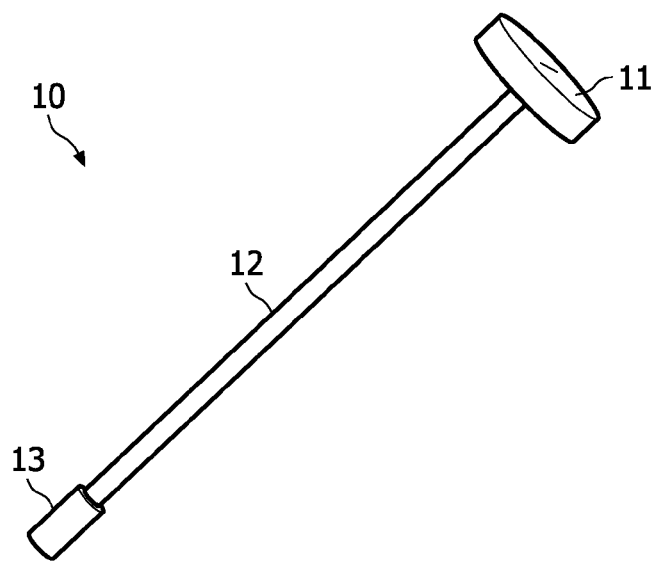
FIG. 1 is an illustration of an example of a DBS system according to prior art.
Figure 2:
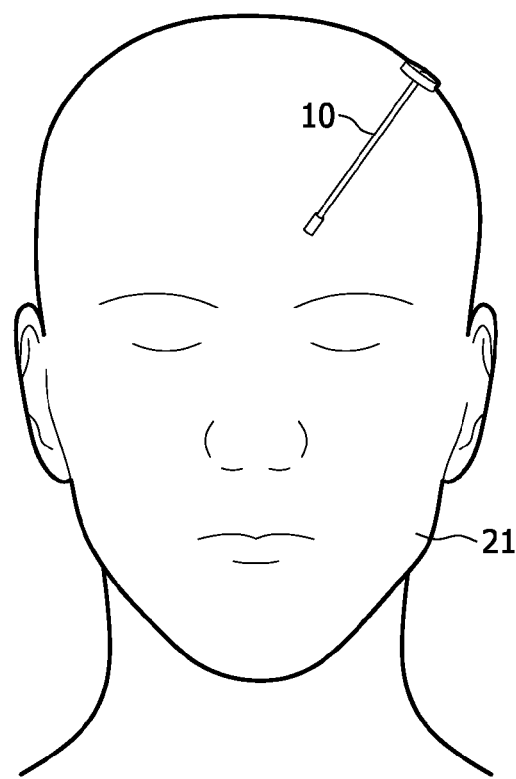
FIG. 2 is an illustration of how a DBS system according to prior art may be positioned in the brain of a person.
Figure 3:
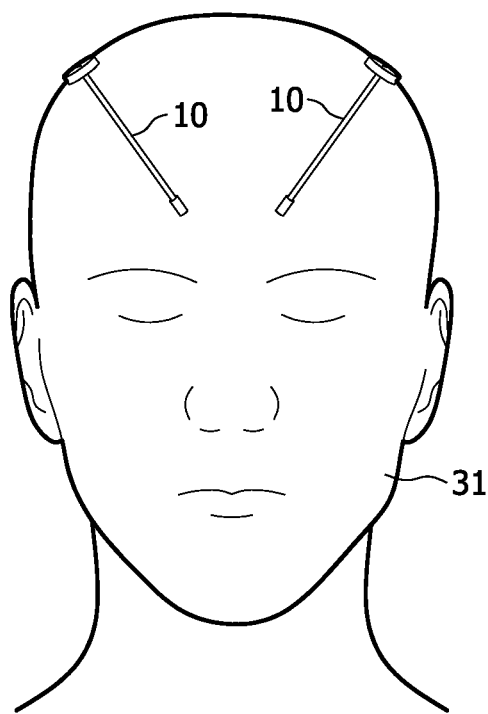
FIG. 3 is an illustration of how two DBS systems may be positioned in the brain of a person, to stimulate both left and right side of the body of the person.
Figure 4:
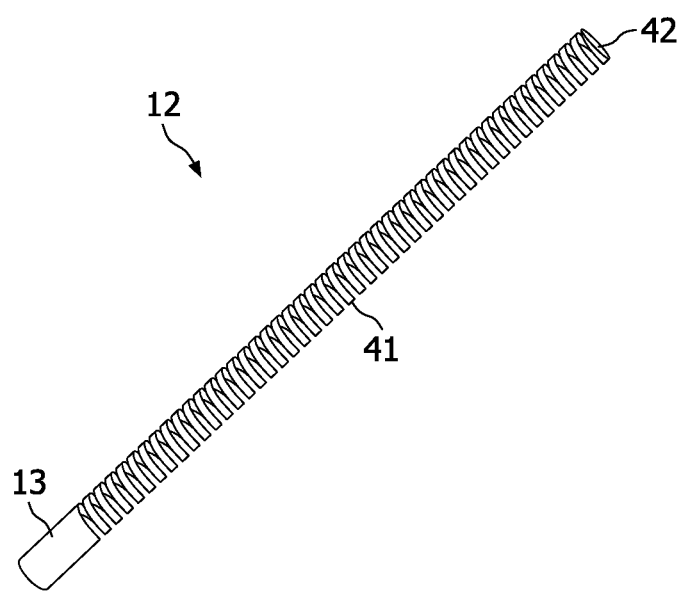
FIG. 4 is an illustration of an internal view of a probe according to prior art.
Figure 5:
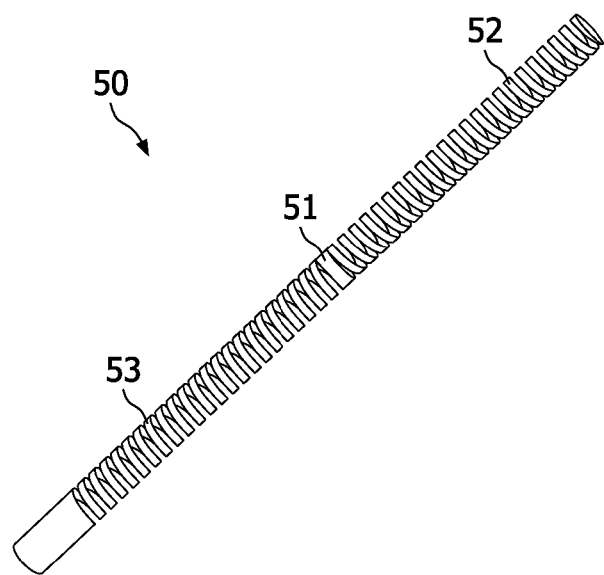
FIG. 5 is an illustration of an internal view of a probe according to an embodiment.

In an embodiment according to FIG. 5, a probe 50 for deep brain stimulation is provided. The probe 50 comprises a number of electrically conducting leads forming a structure 51. The structure 51 comprises at least two interconnected spirals 52, 53, wherein the at least two spirals 52, 53 have different direction of rotation. An advantage of this embodiment is that the structure reduces undesired heating of human tissue, when a person with an implanted DBS probe is exposed to an external magnetic field with altering polarity, such as when performing Magnetic Resonance Imaging (MRI).

Figure 6:
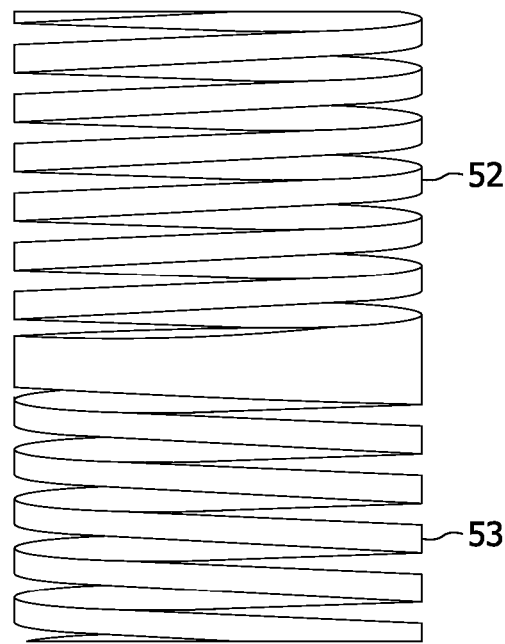
FIG. 6 is an internal illustration of rotation in a part of a probe according to an embodiment.

FIG. 6 illustrates the probe 50 of FIG. 5 in greater detail how the at least two spirals 52, 53 are interconnected according to an embodiment.

Mechanical stability of the structure 51 and of the spirals 52, 53 may be realized in several ways. In an embodiment, the structure 51 is covered with a thermoplastic layer that forms cohesive bonding by heating, e.g. obtained by passing a current through the spirals 52, 53, while the spirals 52, 53 are in contact with a thermoplastic material. The thermoplastic material will melt by the heat of the spiral, and when it cools, it forms a layer around the spirals 52, 53 thus adding stability to the structure 51.

Figure 7:
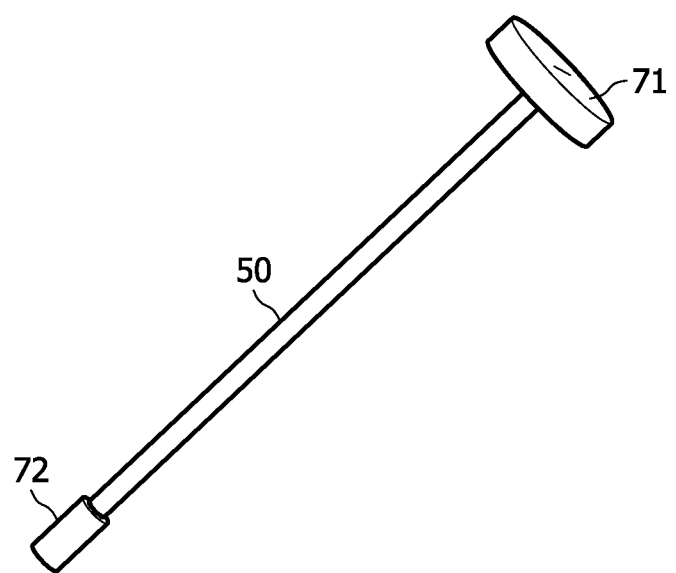
FIG. 7 is an illustration of a probe according to an embodiment, connected to an implanted pulse generator (IPG)

In an embodiment according to FIG. 7 the probe 50 is connected to an implanted pulse generator (IPG) 71 for enabling a flow of current through the electrically conducting leads to the electrodes 72 of the probe 50. An advantage of this embodiment is that the risk of damage of the electronics in the IPG is drastically reduced, when the probe is made subject to an external magnetic field, such as when performing Magnetic Resonance Imaging. Due to the configuration of the structure high voltages and/or currents resulting in the electrically conducting leads, resulting from the external magnetic field, is minimized.

While a single inductor picks up dynamic magnetic fields, a double inductor with oppositely wound loops does not. Thus, no strong currents will arise from an external magnetic field with altering polarity, which may destroy the electronics of the IPG.

In an embodiment, the direction of rotation of the structure is changed halfway.

In an embodiment, the direction of rotation of the structure is changed several times.

In an embodiment, the number of electrically conducting leads is higher than the actual number of leads used for stimulation of tissue. A subset of leads is thus selected for use, and connected to the electrodes of the probe. In an embodiment, wherein the number of electrically conducting leads is 64, 8 leads are selected for connection to the electrodes of the DBS probe. This has the advantage that the probe spatially addresses the best areas in the brain for stimulation.

In an embodiment according to FIG. 8, the electrically conducting leads forming a structure 51 are tracks 54 on a foil 55, such as thin foil having a thickness being less than 1mm. FIG. 8A is showing the foil 55 in a flat configuration, and FIG. 8B is showing the foil 55 configured as interconnected spirals 52, 53, wherein the spirals 52, 53 have different direction of rotation.

The characteristics of the foil will be further described below. An advantage of this embodiment is that it is easier to realize different direction of rotation. Furthermore, the required number of turns may be low when using a foil.

According to another embodiment, the electrically conducting leads are wires. The wires may be separate and insulated. The characteristics of the wires will be further described below. An advantage of using separate and insulated wires is that the wires may be thick, such as around 25 μm, and thus provides a low DC resistance.

In an embodiment according to FIG. 9 it is shown how separate round wires 91 are assembled in a single cable 92. This is a cross section of the cable that may be spiraled or rotated. The configuration results in a dense packing, which results in a relatively small outer dimension of the combined wire.

In an embodiment, the wires are twisted relative to each other before they are spiraled along the probe, to avoid that local parts of the wires have the same relative position to each other in the spiral. This changing of relative positions by twisting of the wires may reduce the pickup of an external magnetic field such as an MRI RF field. Further embodiments are described in the following, non-limiting examples.

Examples

The following examples are made using either the embodiment with foil or the embodiment separate wire. However, this should not be seen as limiting in any way.

At the MRI frequency, typically 40-128 MHz, the spiraled probe has sufficiently high impedance as a result of the higher self-inductance, whereas at the DBS stimulation frequency, typically below a few kHz, the impedance is determined by the DC resistance, which is sufficiently low to limit power dissipation.

According to an embodiment, the overall probe impedance at MRI frequency is above 1 kΩ, while the effective DC resistance is below 100Ω.

According to an embodiment, the overall probe impedance at MRI frequency is above 1 kΩ, while the DC resistance of each lead is below a few kΩ, such as 5 kΩ.

The absolute value Z of the impedance of a spiraled conductor is given by the equation $$Z = \sqrt{R^2 + (2\pi f L)^2}$$

in which R=the (DC) resistance of the spiraled conductor; f=the frequency (which is 64 MHz for a 1.5-T MRI system); and
L=the inductance of the spiraled conductor.

If the required impedance at MRI frequency is above 1 kΩ and the resistance is below 100Ω then the overall impedance of the spiraled conductor equals approximately the impedance of the inductance, which is given by the equation $$Z \approx 2\pi f L$$

The inductance L of a thin-wall finite-length solenoid of radius r and length l made of a round wire is approximated by the equation $$L = \frac{10\pi \mu_0 N^2 r^2}{9r + 10l}$$

in which
N=number of turns;
$\mu_0$=permeability of vacuum=$4\pi \cdot 10^{-7}$ H/m;
r=radius of the solenoid;
l=length of solenoid.

Consequently, the required number of turns N to achieve an impedance Z is given by the equation $$N = \sqrt{\frac{Z}{20\pi^2 \cdot f \cdot \mu_0 \cdot r^2}}$$

According to an embodiment, where
Z=1 kΩ;
r=0.6 mm;
l=10 cm; and
f=64 MHz
it follows that N=420.

However, because of the small dimensions involved when working with DBS probes, it is usual to use very thin leads, such as about 0.1 µm. This makes it more complicated to estimate the impedance with a simple formula, as above. Consequently, 3D electromagnetic simulations were carried out with a varying number of turns of a 10 cm long solenoid. The simulations, which are briefly described below, indicate that for a flat, spiraled conductor, about 250 turns are sufficient.

The 3D electromagnetic simulations were performed according to methods well known to a person skilled in the art, with the 3D electromagnetic simulation program Micro-Wave Studio from CST (www.cst.com). This program is based on the finite integration technique, which represents consistent transformation of the analytical Maxwell equations into a set of matrix equations. The probe was modeled as 10 cm long solenoid of a 0.1 mm wide, perfectly electrically conducting wire. In the simulations, this probe was positioned in a uniform box of 4 cm×4 cm×14 cm with electrical parameters that are representative for those in the human brain at MRI frequency. For an MRI frequency of 64 MHz, the relative dielectric constant was set to 100 and the electrical conductivity was set to 0.5 S/m. At the border of the calculation domain, an incident plane-wave electromagnetic field was imposed with an electrical field component parallel to the axis of the probe. With the 3D simulation program, the current density has been calculated in the material (which represents the brain tissue) surrounding the probe. The maximum current density was taken as evaluation criterion. As stated above, the simulations showed that the maximum current density was reduced strongly when the number of turns was increased to 250 turns over 10 cm. With 250 turns the induced current density near the end of the probe was sufficiently suppressed.

Another factor, which is important to consider, is the wire resistance. This is illustrated in the following example, using an embodiment with foil. The wire resistance may be estimated according to the following. If the wires are in the form of a foil, wrapped spirally around the probe, and
$l_0$=length of the probe;
l=total length of the foil of the coil;
r=probe radius (i.e., coil radius);
w=width of the foil;
p=pitch of the coil;
N=number of turns;
R=resistance of each wire; and
the length of the foil of the coil is calculated by the equation $$l = N\sqrt{(2\pi r)^2 + p^2}$$

In case that pitch p equals the width of the foil w (i.e., every turn is next to the other), then $$l = N\sqrt{(2\pi r)^2 + p^2} = \frac{l_0}{w}\sqrt{(2\pi r)^2 + w^2}$$

Each wire in the foil is a thin-film conductor, whose resistance may be written as $$R = \rho \frac{l}{A} \approx \rho \frac{l}{t\frac{w}{n}} = \frac{\rho n}{t} \cdot \frac{l}{w} \propto \frac{l}{w}$$

where $\rho$=conductivity of the material, t=thickness of the thin film conductor, n=number of conductive wires in each foil.

Furthermore, if the foil is wrapped around the probe in the non-spiral manner (where the wires are straight along the probe), then $$R_0 = \frac{\rho n}{t} \cdot \frac{l_0}{w_0} = \frac{\rho n}{t} \cdot \frac{l_0}{2\pi r}$$

Therefore, $$\frac{R}{R_0} = \frac{l \cdot w_0}{l_0 \cdot w} = \frac{2\pi r}{w} \cdot \sqrt{\left(\frac{2\pi r}{w}\right)^2 + 1}$$

For example, for $l_0$=15 cm, r=0.6 mm, the result according to table 1 is achieved.

TABLE 1

| N | w(mm) | $R/R_0$ |
|---|---|---|
| 250 | 0.6 | 40 |
| 55 | 2.7 | 2.4 |
| 25 | 6 | 0.74 |

Table 1 shows that by wrapping the foil spirally around the probe, the resistance of individual wires does increase with the number of turns. When the number of turns is low, the DC resistance increase is still acceptable for power consumption requirements. However, if 250 turns are needed, then the DC resistance becomes too high.

In an embodiment, 64 separate insulated wires are used instead of foil interconnects. Then a much lower DC resistance may be achieved, as shown below. The higher the number of wires, the more separate electrodes can be addressed. This allows the physician to better determine which parts of the brain tissue will be stimulated. Thus, the number of wires used may vary, but they must be sufficiently many to provide enough separate electrodes, while simultaneously sufficiently few to provide a low DC resistance.

For a 15 cm long probe with 250 turns, the pitch is 600 μm. If each separate wire is a gold micro wire with a diameter of 25 μm, 64 wires may easily fit in a cable with a diameter of 600 μm. The cable may be about 950 mm long. The DC resistance of each wire is calculated with the equation $$R = \rho \frac{l}{A} = 2.2 \times 10^{-8} \times \frac{0.95}{\pi (12.5 \times 10^{-6})^2} = 42 \, \Omega$$

which fulfils the resistance requirement to reach a practical battery life.

Accordingly, in an embodiment, the spiral comprises 64 parallel wires. The wires may be separate and insulated. The wires may be squared or circular.

In an embodiment, only two groups of 8 parallel wires are electrically driven by two circuits in the IPG. The remaining wires are passively connected to the ground of the IPG, thus forming an electric circuit. In an embodiment, the remaining wires are connected to the IPG via a resistance.

According to an embodiment, the spiral comprises a foil with 64 parallel tracks. An advantage with this is that the spiral is easy to manufacture.

In an embodiment, the probe with a number of electrically conducting leads forming a spiral wherein the rotation of the spiral is reversed is provided may be comprised in a system. Such system may be e.g. a system for DBS, pacemaker, muscle stimulation or gastro-intestinal stimulation. Features according to other embodiments described above may also be comprised in the system.

The probe may the probe with a number of electrically conducting leads forming a spiral wherein the rotation of the spiral is reversed is provided may be used for deep brain stimulation. Furthermore, the probe may be used for pacemaker stimulation, for muscle stimulation of for gastro-intestinal stimulation.

The DBS probe may be constructed either with a separate return electrode, or the housing of the IPG may serve as the electrical contact to the brain tissue for return current. Thus when the probe according to an embodiment is used, the current is flowing from the IPG through the spiral, via the contacts at the end of the probe, through the human tissue and back to the return electrode or the IPG housing.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A probe for deep brain stimulation, comprising:
a plurality of electrically conducting leads forming a structure having a longitudinal axis and comprising at least two end-to-end interconnected spirals,
wherein the structure comprises a foil and the electrically conducting leads comprise tracks on the foil,
wherein the at least two end-to-end interconnected spirals extend around the longitudinal axis and have different directions of rotation such that, when the spirals are subjected to an external magnetic field, levels of currents induced in the spirals by the external magnetic field are reduced, and
wherein the structure has a single, continuous, non-overlapping outer surface that extends from a proximal end of one of the at least two end-to-end interconnected spirals to at least a distal end of another one of the at least two end-to-end interconnected spirals.

2. The probe according to claim 1, wherein at least one electrically conducting lead at a first end is configured to be connected to a power source to enable an electric current to flow through the electrically conducting leads.

3. The probe according to claim 1, wherein the direction of rotation of the at least two end-to-end interconnected spirals changes halfway along a length of the structure.

4. The probe according to claim 1, wherein the direction of rotation of the at least two end-to-end interconnected spirals changes several times along a length of the structure.

5. The probe according to claim 1, wherein a number of electrically conducting leads included in the plurality of electrically conducting leads is higher than the actual number of leads used for stimulation of tissue.

6. The probe according to claim 1, wherein the structure includes an interconnecting section that extends between, but does not overlap, two of the at least two end-to-end interconnected spirals.

7. The probe according to claim 1, wherein the single, continuous, non-overlapping outer surface extends from one terminal end of the structure to another terminal end of the structure.

8. The probe according to claim 1, wherein each of the tracks on the foil comprise a thin-film conductor.

9. A system comprising:
a probe comprising a plurality of electrically conducting leads forming a structure having a longitudinal axis and comprising at least two end-to-end interconnected spirals, wherein the structure comprises a foil and the electrically conducting leads comprise tracks on the foil, wherein the at least two end-to-end interconnected spirals extend around the longitudinal axis and have different directions of rotation such that, when the spirals are subjected to an external magnetic field, levels of currents induced in the spirals by the external magnetic field are reduced, and wherein the structure has a single, continuous, non-overlapping outer surface that extends from a proximal end of one of the at least two end-to-end interconnected spirals to at least a distal end of another one of the at least two end-to-end interconnected spirals;

an electrode coupled to one or more of the electrically conducting leads; and a stimulation generator configured to deliver electrical stimulation via the electrode.

10. The system of claim 9, wherein probe is configured for deep brain stimulation.

11. The system of claim 9, wherein the probe is configured for cardiac pacemaking.

12. The system of claim 9, wherein the probe is configured for muscle stimulation.

13. The system of claim 9, wherein the probe is configured for gastro-intestinal stimulation.

14. A method for deep brain stimulation, the method comprising:

delivering, by a stimulation generator and via an electrode coupled to one or more of a plurality of electrically conducting leads of a probe, electrical stimulation, wherein the plurality of electrically conducting leads form a structure having a longitudinal axis and comprising at least two end-to-end interconnected spirals, wherein the structure comprises a foil and the electrically conducting leads comprise tracks on the foil, wherein the at least two end-to-end interconnected spirals extend around the longitudinal axis and have different directions of rotation such that, when the spirals are subjected to an external magnetic field, levels of currents induced in the spirals by the external magnetic field are reduced, and wherein the structure has a single, continuous, non-overlapping outer surface that extends from a proximal end of one of the at least two end-to-end interconnected spirals to at least a distal end of another one of the at least two end-to-end interconnected spirals.

15. The method of claim 14, wherein the structure includes an interconnecting section that extends between, but does not overlap, two of the at least two end-to-end interconnected spirals.

16. The method of claim 14, wherein a number of electrically conducting leads included in the plurality of electrically conducting leads is higher than the actual number of leads used to deliver the electrical stimulation.

17. The method of claim 14, wherein the single, continuous, non-overlapping outer surface extends from one terminal end of the structure to another terminal end of the structure.

18. The method of claim 14, wherein each of the tracks on the foil comprise a thin-film conductor.

* * * * *